(12) United States Patent
Sharpless (10) Patent No.: US 11,426,605 B2
(45) Date of Patent: Aug. 30, 2022

(54) SYSTEMS AND METHODS FOR REDUCING A RADIAL DISTANCE OF A COLLIMATOR ASSEMBLY OCCUPYING

(71) Applicant: UIH AMERICA, INC., Houston, TX (US)

(72) Inventor: Ronald Sharpless, Houston, TX (US)

(73) Assignee: UIH AMERICA, INC., Houston, TX (US)

(*) Notice: Subject to any disclaimer, the term of this patent is extended or adjusted under 35 U.S.C. 154(b) by 17 days.

(21) Appl. No.: 17/067,906

(22) Filed: Oct. 12, 2020

(65) Prior Publication Data

US 2021/0023396 A1 Jan. 28, 2021

Related U.S. Application Data

(63) Continuation of application No. 16/147,730, filed on Sep. 29, 2018, now Pat. No. 10,799,717.

(51) Int. Cl.
*A61N 5/10* (2006.01)
*G16H 20/40* (2018.01)

(52) U.S. Cl.
CPC ........... *A61N 5/1045* (2013.01); *A61N 5/103* (2013.01); *A61N 5/1048* (2013.01); *A61N 5/1007* (2013.01); *A61N 2005/1095* (2013.01); *G16H 20/40* (2018.01)

(58) Field of Classification Search
CPC .... A61N 5/1007; A61N 5/103; A61N 5/1045; A61N 5/1048; A61N 2005/1095; G16H 20/40
See application file for complete search history.

(56) References Cited

U.S. PATENT DOCUMENTS

| | | | |
|---|---|---|---|
| 4,463,266 | A | 7/1984 | Brahme |
| 5,012,506 | A | 4/1991 | Span et al. |
| 2011/0293071 | A1 | 12/2011 | Torsti et al. |
| 2013/0261430 | A1 | 10/2013 | Uhlemann |
| 2015/0105604 | A1 | 4/2015 | Liu et al. |
| 2017/0084359 | A1 | 3/2017 | Constantin et al. |
| 2017/0119340 | A1 | 5/2017 | Nakai et al. |
| 2017/0151444 | A1 | 6/2017 | Li et al. |

*Primary Examiner* — Mark R Gaworecki
(74) *Attorney, Agent, or Firm* — Metis IP LLC (57) ABSTRACT

A device may include a collimator positioned between a radiation source of a scanner and a bore of the scanner. The bore may include a detecting region configured to accommodate a subject. The collimator may be configured to prevent at least one portion of radiation rays emitted from the radiation source from being incident on the subject. The device may further include a first filter and a second filter. The first filter may be positioned between the radiation source and the collimator. The second filter may be positioned between the collimator and the bore. The first filter and the second filter may be configured to adjust a distribution of radiation impinging upon the subject.

20 Claims, 6 Drawing Sheets

SYSTEMS AND METHODS FOR REDUCING A RADIAL DISTANCE OF A COLLIMATOR ASSEMBLY OCCUPYING

CROSS-REFERENCE TO RELATED APPLICATIONS

This present application is a continuation of U.S. patent application Ser. No. 16/147,730, filed on Sep. 29, 2018, the contents of which are hereby incorporated by reference.

TECHNICAL FIELD

The present disclosure generally relates to medical imaging systems, and in particular, the medical imaging systems having a collimator assembly with a short occupied radial distance.

BACKGROUND

High energy beams such as x-rays are widely used for medical diagnosis or radiation therapy in, for example, computed tomography (CT) systems, positron emission tomography (PET) systems, single photon emission computed tomography (SPECT) systems. In many of these applications, a collimator is often utilized to limit or collimate high energy beams (e.g., X-rays) emitted from a radiation source. For example, in a CT system, a collimator assembly may be used to collimate X-ray beams emitted from an X-ray source, and the collimated X-ray beams may impinge upon a subject to be scanned (e.g., a patient). The collimator assembly may reside between the X-ray source and the bore accommodating the subject. The X-ray efficiency in such configuration may be inversely proportional to the squared distance between the subject and X-ray source. Additionally, a larger bore, which accommodates the subject, is more desirable because it may be easier for a patient to get into the bore. The smaller a radial distance of a collimator assembly occupying, the smaller the distance between the subject and X-ray source may be, and the larger the bore may be designed to be. Therefore, it is desirable to provide systems for reducing the occupied radial distance of the collimator assembly as small as possible, that can make system purchase, operation, and maintenance costs lower.

SUMMARY

In one aspect of the present disclosure, a device is provided. The device may include a collimator positioned between a radiation source of a scanner and a bore of the scanner. The bore may include a detecting region configured to accommodate a subject. The collimator may be configured to prevent at least one portion of radiation rays emitted from the radiation source from being incident on the subject. The device may further include a first filter and a second filter. The first filter may be positioned between the radiation source and the collimator. The second filter may be positioned between the collimator and the bore. The first filter and the second filter may be configured to adjust a distribution of radiation impinging upon the subject.

In some embodiments, the second filter may include a first surface facing the collimator. The shape of the first surface may conform to a shape of the collimator.

In some embodiments, the second filter may include a second surface facing the bore. The shape of the second surface may conform to a shape of the bore.

In some embodiments, the second filter may be integrated into a cover for encompassing the bore.

In some embodiments, the first filter may include a surface facing the collimator. The shape of the surface facing the collimator may conform to a shape of the collimator.

In some embodiments, the first filter may include at least one of a bowtie filter or a wedge filter.

In some embodiments, the second filter may include at least one of a bowtie filter or a wedge filter.

In some embodiments, the first filter may include a first material, and the second filter may include a second material. The first material or the second material may include at least one of plastic, graphite, or aluminum.

In some embodiments, the first material may be different from the second material.

In some embodiments, the first material may be same as the second material.

In some embodiments, the device may further include a measurement component configured to determine at least one of an intensity of radiation beams that reaches the first filter or a location of the radiation source.

In some embodiments, the first filter may have a surface facing the radiation source. The surface may form a concave. The measurement component may be located in the concave.

In some embodiments, the device may further include a motion component configured to move at least one of the collimator, the first filter, or the second filter.

In some embodiments, the device may further include a third filter. The third filter may be a flat filter.

In another aspect of the present disclosure, a system for reducing a radial distance of a collimator assembly occupying is provided. The system may include a scanner including a radiation source and a bore. The system may also include a collimator assembly positioned between the radiation source and the bore of the scanner. The bore may include a detecting region configured to accommodate a subject. The collimator assembly may include a collimator positioned between the radiation source and the bore. The collimator may be configured to prevent at least one portion of radiation rays emitted from the radiation source from being incident on the subject. The collimator assembly may further include a first filter and a second filter. The first filter may be positioned between the radiation source and the collimator. The second filter may be positioned between the collimator and the bore. The first filter and the second filter may be configured to adjust a distribution of radiation impinging upon the subject.

In some embodiments, the second filter may include a first surface facing the collimator. The shape of the first surface may conform to a shape of the collimator.

In some embodiments, the second filter may further include a second surface facing the bore. The shape of the second surface may conform to a shape of the bore.

In some embodiments, the first filter may include a surface facing the collimator. The shape of the surface facing to the collimator may conform to a shape of the collimator.

In some embodiments, the first filter may include at least one of a bowtie filter or a wedge filter.

In some embodiments, the second filter may include at least one of a bowtie filter or a wedge filter.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is to describe particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "module," and/or "block" used herein are one method to distinguish different components, elements, parts, section or assembly of different level in ascending order. However, the terms may be displaced by another expression if they achieve the same purpose.

The term "module," or "block," as used herein, refers to logic embodied in hardware or firmware, or to a collection of software instructions. A module or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an Electrically Programmable Read-Only-Memory (EPROM). It will be further appreciated that hardware modules/units/blocks may be included in connected logic components, such as gates and flip-flops, and/or can be included in programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a module or block is referred to as being "connected to," or "coupled to," another module, or block, it may be directly connected or coupled to, or communicate with the other module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The present disclosure provides medical diagnosis and/or treatment systems having a collimator assembly with a short occupied radial distance. The systems may include an adjustable aperture device (also referred to herein as a collimator) positioned between the radiation source and the bore of a scanner. The bore may include a detecting region configured to accommodate a subject to be radiated such as a patient. The collimator may be configured to limit at least some portion of radiation rays emitted from the radiation source so that only those traveling parallel to a specified direction are allowed to pass through and reach the subject and the detectors. The systems may also include a first filter positioned between the radiation source and the collimator, and a second filter positioned between the collimator and the bore. The first filter and the second filter may be configured to adjust the distribution of the radiation impinging upon the subject.

The following descriptions are provided to help better understand the systems and/or devices. This is not intended to limit the scope the present disclosure. For persons having ordinary skills in the art, a certain amount of variations, changes, and/or modifications may be deducted under the guidance of the present disclosure. Those variations, changes, and/or modifications do not depart from the scope of the present disclosure.

Figure 1:
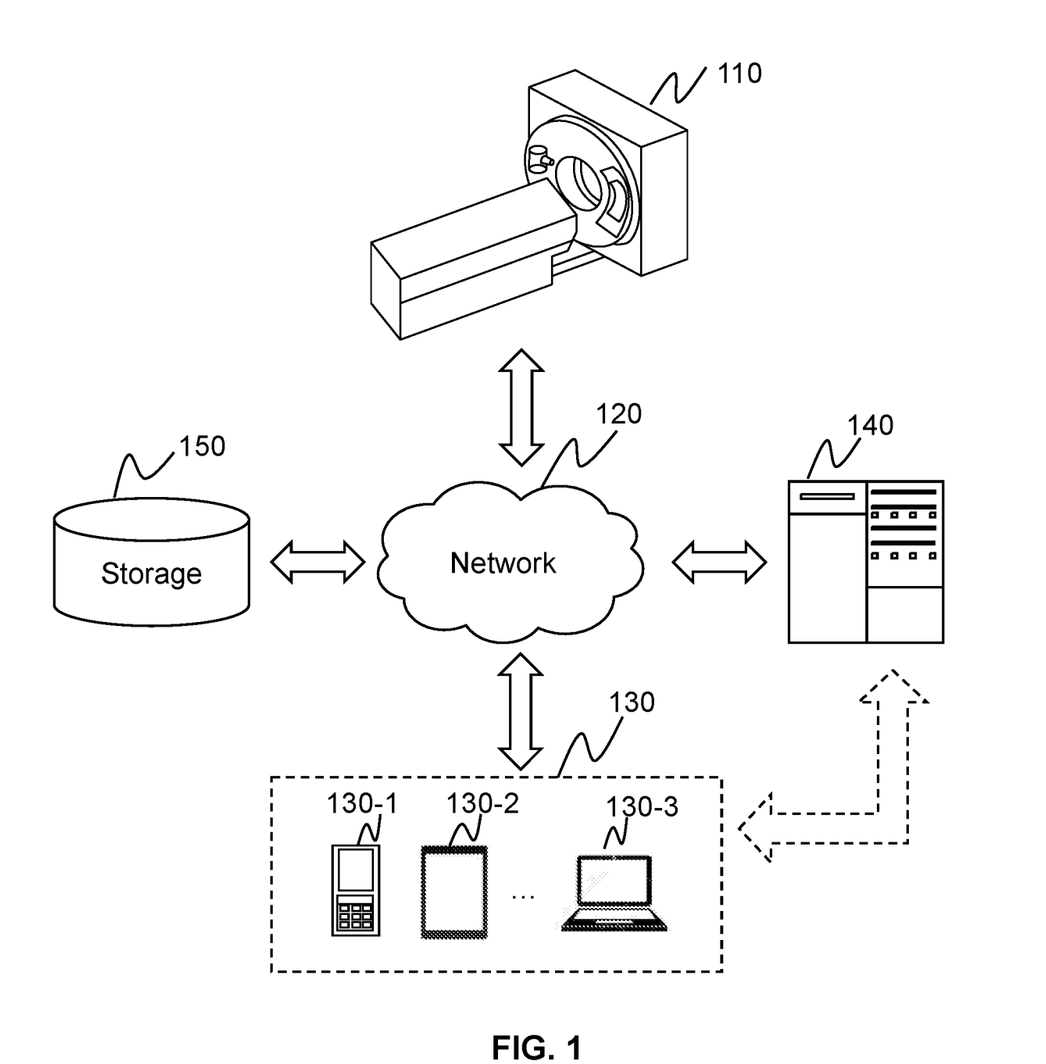
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. As shown in FIG. 1, the imaging system 100 may include a scanner 110, a network 120, a terminal 130, a processing device 140, and a storage 150. In some embodiments, the scanner 110, the processing device 140, the storage 150, and/or the terminal 130 may be connected to and/or communicate with each other via a wireless connection (e.g., the network 120), a wired connection, or a combination thereof. The connections between the components in the imaging system 100 may vary. For example, the scanner 110 may be connected to the processing device 140 through the network 120, as illustrated in FIG. 1. Alternatively, the scanner 110 may be connected to the processing device 140 directly, via, for example, data cable. The storage 150 may be connected to the processing device 140 through the network 120 or directly via data cable. The terminal 130 may be connected to the processing device 140 through the network 120 or directly.

The scanner 110 may scan a subject and generate imaging data. The subject scanned may be biological or non-biological. For example, the subject may include a patient, a man-made object (e.g., a phantom for calibration), etc. As another example, the subject may include a specific portion, organ, and/or tissue of a patient. For instance, the subject may include the patient's head, brain, neck, body, shoulder, arm, thorax, cardiac, stomach, blood vessel, soft tissue, knee, feet, or the like, or any combination thereof.

The scanner 110 may include a CT scanner, a PET scanner, a SPECT scanner, an X-ray or gamma ray scanner, a multi-modality scanner, or the like, or any combination thereof. Exemplary multi-modality scanner may include a CT-PET scanner.

The scanner 110 may send the data generated to the storage 150, the processing device 140, or the terminal 130 via the network 120. For example, the scanner 110 may be configured to scan the subject (e.g., a patient) to obtain imaging data based on a scanning of the subject. In some embodiments, the scanner 110 may include a gantry, a radiation source, a collimator assembly, a detector, a table, or the like, or any combination thereof. The gantry may provide support for one or more components of the scanner 110. The gantry may include a bore configured to accommodate a subject (e.g., a patient) for scanning. To perform a scan (or during the radiation treatment), the radiation source 220 may emit radiation beams (e.g., X-rays) toward a subject to be scanned. The collimator assembly may be configured to filter and/or regulate the radiation beams emitted from the radiation source. The radiation beams may impinge upon the subject and be detected by the detector for generating a medical image corresponding to the subject. The collimator assembly may be located between the radiation source and the bore. The height (or the thickness) of the collimator assembly may have an impact on the radial distance between the radiation source and the bore. Generally, the shorter the height of the collimator assembly, the smaller the radial distance the collimator assembly occupying and the smaller the radial distance between the radiation source and the bore. The collimator assembly may include a first filter, an aperture device and the second filter. The shape of a surface of the first filter, which faces the aperture device, may conform to the shape of the aperture device. The shape of a surface of the second filter, which faces the bore of the scanner may conform to the shape of the bore. The collimator assembly may occupy a shorter radial distance, which leads to a higher radiation efficiency.

The network 120 may include any suitable network that can facilitate the exchange of information and/or data for the imaging system 100. In some embodiments, one or more components of the imaging system 100 (e.g., the scanner 110, the terminal 130, the processing device 140, the storage 150) may communicate information and/or data with one or more other components of the imaging system 100 via the network 120. For example, the processing device 140 may obtain the data for imaging from the scanner 110 via the network 120. As another example, the processing device 140 may obtain user instructions from the terminal 130 via the network 120. The network 120 may be and/or include a public network (e.g., the Internet), a private network (e.g., a local area network (LAN), a wide area network (WAN))), a wired network (e.g., an Ethernet network), a wireless network (e.g., an 802.11 network, a Wi-Fi network), a cellular network (e.g., a Long-Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near-field communication (NFC) network, or the like, or any combination thereof. In some embodiments, the network 120 may include one or more network access points. For example, the network 120 may include wired and/or wireless network access points such as base stations and/or internet exchange points through which one or more components of the Imaging system 100 may be connected to the network 120 to exchange data and/or information. Merely by way of example, the processing device 140 may be configured to obtain a 3D image from the storage 150 via the network 120.

The terminal 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, a smart accessory, or the like, or any combination thereof. In some embodiments, the mobile device may include a mobile phone, a personal digital assistant (PDA), a laptop, a tablet computer, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140. Merely by way of example, the terminal 130 may be configured to display a 3D image. The terminal 130 may also be configured to transmit an instruction for scanning a subject to the scanner 110. The terminal 130 may further be configured to transmit an instruction for measuring a radiation ray intensity and/or the location of the radiation source.

The processing device 140 may process data and/or information obtained from the scanner 110, the terminal 130, and/or the storage 150. For example, the processing device 140 may obtain the data for imaging from the scanner 110 and/or the storage 150. In some embodiments, the processing device 140 may be a workstation or server. For example, the processing device 140 may be a single server or a server group. The server group may be centralized or distributed. In some embodiments, the processing device 140 may be local or remote. For example, the processing device 140 may access information and/or data stored in the scanner 110, the terminal 130, and/or the storage 150 via the network 120. As another example, the processing device 140 may be directly connected to the scanner 110, the terminal 130 and/or the storage 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage 150 may store data, instructions, and/or any other information. In some embodiments, the storage 150 may store data obtained from the terminal 130 and/or the processing device 140. In some embodiments, the storage 150 may store data and/or instructions that the processing device 140 and/or the terminal 130 may execute or use to perform exemplary methods described in the present disclosure. In some embodiments, the storage 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. The storage 150 may be configured to store information and/or data associated with the scanner 110 and/or the subject. For example, the storage 150 may be configured to store instructions for controlling a component (e.g., a collimator assembly) of the scanner 110. As another example, the storage 150 may be configured to store image data of the subject detected by the scanner 110.

In some embodiments, the storage 150 may be connected to the network 120 to communicate with one or more other components of the imaging system 100 (e.g., the processing device 140, the terminal 130). One or more components of the imaging system 100 may access the data or instructions stored in the storage 150 via the network 120. In some embodiments, the storage 150 may be directly connected to or communicate with one or more other components in the imaging system 100 (e.g., the scanner 110, the processing device 140, the terminal 130). In some embodiments, the storage 150 may be part of the processing device 140. Merely by way of example, the storage 150 may be configured to store a 3D image.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage 150 may be a data storage including cloud computing platforms, such as, public cloud, private cloud, community, and hybrid clouds, etc. However, those variations and modifications do not depart the scope of the present disclosure.

Figure 2:
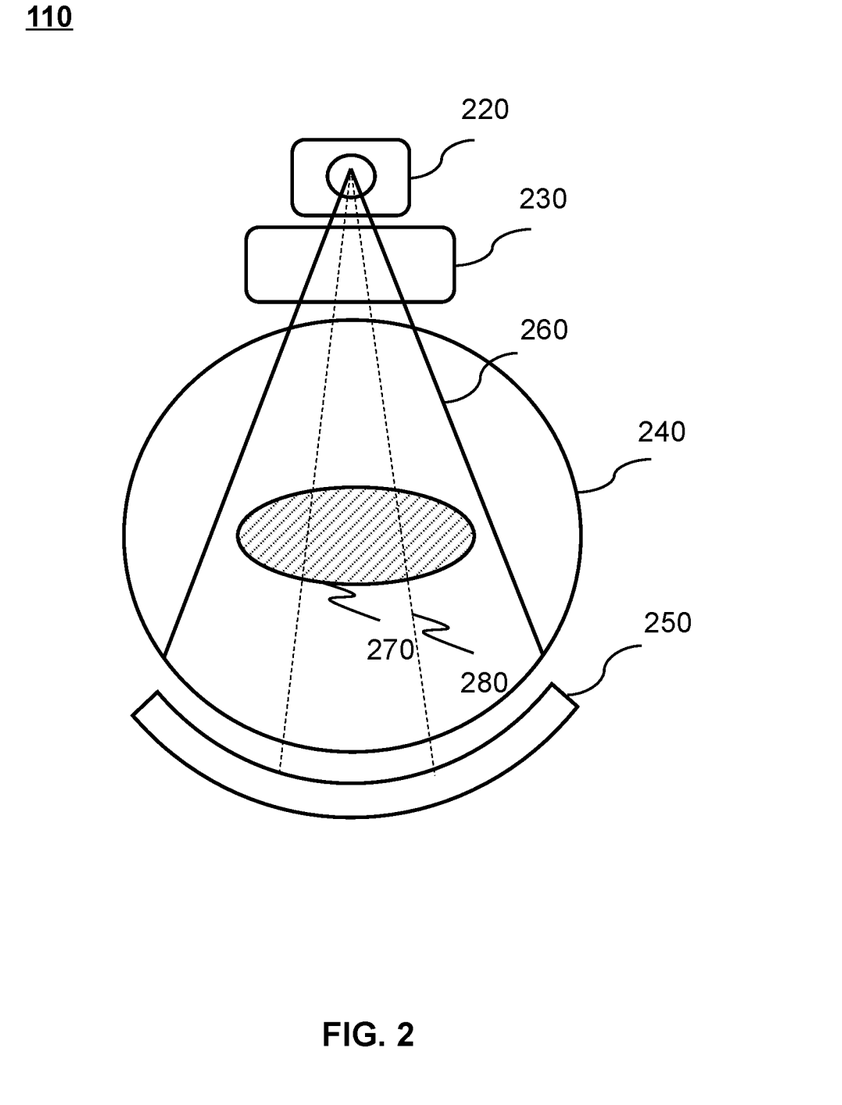
FIG. 2 is a schematic diagram illustrating an exemplary scanner according to some embodiments of the present disclosure.

FIG. 2 is a schematic diagram illustrating an exemplary scanner 110 according to some embodiments of the present disclosure. For brevity, a CT scanner is taken as an example of the scanner 110 for the purposes of illustration. As illustrated in FIG. 2, the scanner 110 may include a gantry (not shown), a radiation source 220, a collimator assembly 230, a bore 240, a detector 250, a table (not shown), etc.

The gantry may support the radiation source 220 and the detector 250. In some embodiments, the radiation source 220 and/or the detector 250 may be configured on the gantry. In some embodiments, the radiation source 220 and/or the detector 250 may move or rotate relative to the gantry. For example, the gantry may rotate around a rotation axis. The radiation source 220 and/or the detector 250 may rotate with the rotation of the gantry. The rotation axis may coincide with the centerline axis of the bore.

The radiation source 220 may include an imaging source, a treatment source (e.g., X-ray source, etc.), or a combination thereof. To perform a scan (or during the radiation treatment), the radiation source 220 may emit radiation beams (e.g., X-rays) such as rays 260 and rays 280 toward a subject 270. The subject 270 may be placed on the table in the bore positioned at or near the center of the gantry. At least part of the radiation beams that the radiation source 220 emits (e.g., the rays 280), after being attenuated by the subject 270, may impinge upon the detector 250 and be measured by the detector 250.

The detector 250 may produce electrical signals indicative of the radiation beams received. The detector 250 may include one or more detector modules having an arcuate structure including a plurality of pixels and/or channels. The pixels may measure radiation beams and generate signals. The pixels may be arranged in a single row, two rows, or any other number of rows. The signals may be generated by respective pixels in response to the radiation beams measured. The signals may include different attributes (e.g., a radiation amplitude). For example, a signal may include a lower radiation amplitude when a radiation beam is measured traversing a higher density tissue (e.g., a bone tissue). The detector 250 may have any suitable shape. For example, the shape of the detector 250 may be flat, arc-shaped, circular, or the like, or a combination thereof. The fan angle of an arc-shaped detector array may have any suitable value. For example, the fan angle may be in the range from 0° to 360°, from 30° to 270°, from 45° to 300°, etc. The fan angle may be fixed or adjustable according to different conditions including, for example, a desired resolution of an image, the size of an image, the sensitivity of the detector, the stability of the detector, or the like, or a combination thereof.

The collimator assembly 230 may include a plurality of collimator elements including, for example, at least one filter, an adjustable aperture device (also referred to herein as a collimator), a measurement device, or the like, or a combination thereof. The filter(s) may include a flat filter, a bowtie filter, a wedge filter, or the like, or any combination thereof. The filter(s) may be configured to adjust at least one portion of radiation rays and/or energy of radiation rays to reduce the energy of radiation rays, create a uniform radiation intensity, or the like, or any combination thereof. For example, a flat filter may be configured to remove particular energies of X-rays that are damaging to the subject and/or are not good for imaging. As another example, with a bowtie filter, a lower dose of X-rays may be needed for imaging.

The adjustable aperture device may be configured to shape radiation beams to a predetermined shape (or profile), for example, fan-shaped radiation beams. In some embodiments, the predetermined shape may be different according to different anatomy (e.g., head, chest, etc.). The predetermined shape may be set by a user or according to the default settings of the imaging system 100 (e.g., a scanning protocol, a treatment plan, etc.).

The measurement device may be configured to determine an intensity of radiation beams and/or the location of the radiation source. In some embodiments, the measurement device may include an intensity sensor (e.g., a radiation power meter, or a radiation energy meter), a position sensor (e.g., a position sensitive detector), or the like, or any combination thereof. For example, the radiation power meter may include a probe, for example, a thermal probe and/or a photodiode probe, to detect the radiation beams it receives from the radiation source. As another example, the position sensitive detector may include a photoconductive detector, a photovoltaic detector, a Schottky barrier diodes detector, etc. In some embodiments, the measurement component may include one or more detectors that may be similar or same as the detector 250. For example, the measurement component may include one single detector configured to detect the intensity of radiation beams. As another example, the measurement component may include several detectors arranged in an array or matrix. The several detectors arranged in an array or matrix may be configured to measure both intensity of radiation beams and the location of radiation source.

The collimator assembly 230 may be located between the radiation source 220 and the bore 240. The height (or the thickness) of the collimator assembly 230 may have an impact on the radial distance between the radiation source 220 and the bore. Generally, the greater the height of the collimator assembly 230, the larger the radial distance the collimator assembly 230 occupying and the larger the radial distance between the radiation source 220 and the bore 240. Conversely, a shorter height of the collimator assembly 230 may result in a shorter radial distance between the radiation source 220 and the bore 240, which leads to a higher radiation efficiency. As used herein, a radial distance between the radiation source 220 and the bore 240 refers to a distance from the center of the radiation source 220 to the center of the bore 240. The height of the collimator assembly 230 refers to the distance between the top surface of the collimator assembly 230 and the bottom surface of the collimator assembly 230 along the center axis of the collimator assembly 230 in a radial direction. The center axis of the collimator assembly 230 traverses the center of the radiation source 220 and the center of the bore 240. In some embodiments, the collimator assembly 230 may include a first filter, an aperture device, and the second filter. The first filter and/or the second filter may include at least one bowtie filter. The shape of a surface of the first filter, which faces the adjustable aperture device, may conform to the shape of the adjustable aperture device. The shape of a surface of the second filter, which faces the bore 240 of the scanner 110 may conform to the shape of the bore. And then the collimator assembly 230 may occupy a shorter radial distance which leads to a higher radiation efficiency. Detailed descriptions of the collimator assembly 230 may be found elsewhere of the present disclosure (e.g., FIGS. 3-6 and the descriptions thereof).

The descriptions above are intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. In some embodiments, the scanner 110 may further include an anti-scatter grid apparatus configured between the bore 240 and the detector 250. However, those variations and modifications do not depart the scope of the present disclosure.

Figure 3:
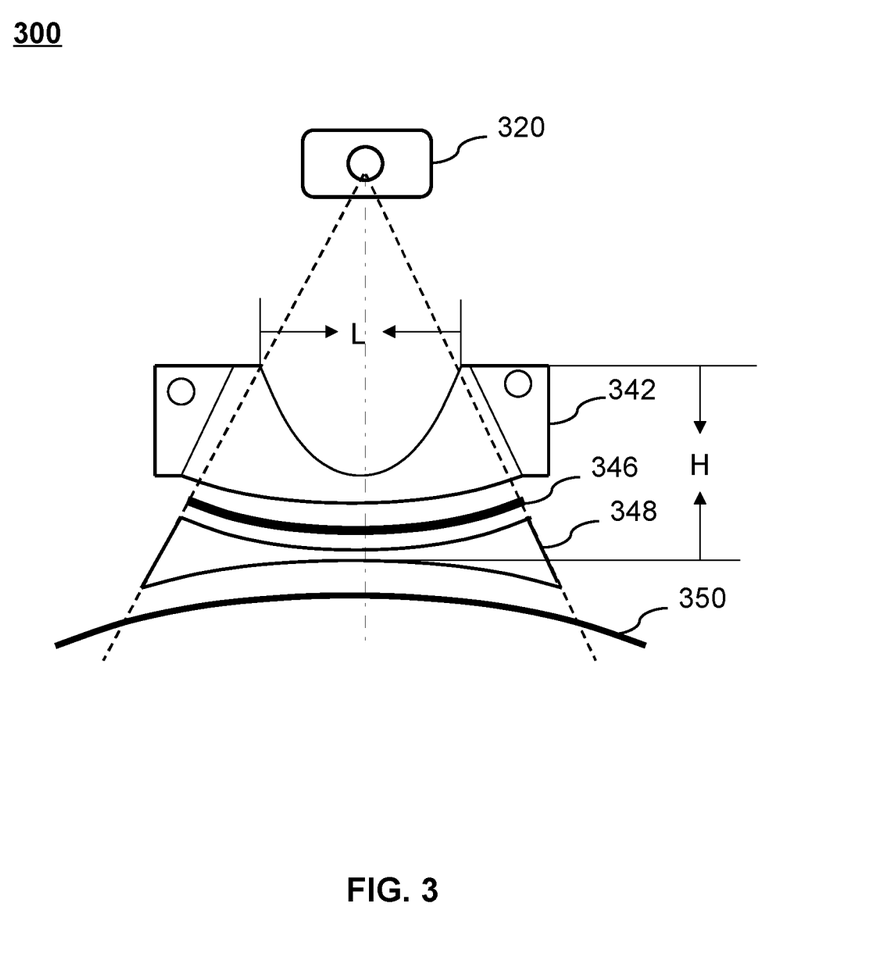
FIG. 3 is a schematic diagram illustrating an exemplary collimator assembly according to some embodiments of the present disclosure.

FIG. 3 is a schematic diagram illustrating an exemplary collimator assembly 300 according to some embodiments of the present disclosure. For brevity, a radiation source 320 and a bore 350 may be used for describing the collimator assembly 300. As illustrated in FIG. 3, the collimator assembly 300 may include a first filter 342, an aperture device 346, and a second filter 348. In some embodiments, the first filter 342, the aperture device 346, and/or the second filter 348 may be housed in a carriage (not shown in FIG. 3) and detachable from the carriage. In some embodiments, the first filter 342, the aperture device 346, and/or the second filter 348 may move or rotate in the carriage according to a movement component. For example, the aperture device 346 may rotate in the carriage according to a clinical condition associated with a subject to be scanned (e.g., a patient).

The first filter 342 may be configured to adjust the distribution of radiation rays that impinge upon a subject. For example, the first filter 342 may lower the dose of X-rays that is needed for imaging. As another example, the first filter 342 may decrease dose X-rays to the subject for treating. The first filter 342 may include a bowtie filter and/or a wedge filter. In some embodiments, the thickness of the first filter 342 may decrease along the direction from an edge to the center of the first filter 342. For example, if most of the imaging mass (or a region of interest) of the subject is located at the center of the bore 350, the thickness of the subject may decrease from the center of the subject to an edge of the subject. Therefore, the thickness of the first filter 342 at the center may be the minimal, and the thickness the first filter 342 at the edge may be greater than the thickness of the first filter 342 at the center. In some embodiments, the first filter 342 may include a first surface facing the radiation source 320 and a second surface facing the aperture device 346. The shape of the first surface of the first filter 342 (i.e., the top surface of the first filter 342) may be in accordance with the size and/or shape of a subject or a region of the subject to be scanned. The first surface may form a concave as shown in FIG. 3. In some embodiments, the concave may be configured to accommodate other components of the collimator assembly 300, such as an X-ray intensity measurement device and/or an attenuating material. The shape of the concave or the first surface may be determined based on a clinical condition such as the shape of the subject (or a region thereof) to be scanned. For example, the length of the first surface of the first filter 342 (denoted as L shown in FIG. 3) corresponding to the head of a human body may be less than that of the first filter 342 corresponding to the chest of the body. In some embodiments, the length of the first surface of the first filter 342 may be adjusted according to the size and/or shape of the subject (or a region thereof). For example, the first surface of the first filter 342 may be extensible or elastic. Merely by way of example, if the head of the subject is to be scanned, the first filter 342 may be controlled by, for example, the processing device 140, to adjust the first surface to a shorter length in comparison with scanning the chest of the subject. As another example, there may be a plurality of first filters 342 having different combinations of various sized first surfaces and second surfaces available. When a subject with a specific size and/or shape, a first filter 342 having a first surface with suitable size may be selected to be placed in the collimator assembly 300.

The shape of the second surface of the first filter 342, which faces the aperture device 346, may conform to the shape of the aperture device 346. For example, if the shape of the aperture device 346 includes an arc-shape (e.g., the arc-shape shown in FIG. 3), the shape of the second surface of the first filter 342 (i.e., the bottom surface of the first filter 342) may include an arc-shape according to the arc-shape of the aperture device 346. As another example, if the shape of the aperture device includes a flat shape (e.g., the flat shape of the aperture device 446 illustrated in FIG. 4), the shape of the second surface may include a flat shape in accordance with the flat shape of the aperture device (i.e., the bottom surface of the first filter 442 shown in FIG. 4). In some embodiments, the first filter 342 may include or be made of a first material capable of absorbing radiation, which may include at least one of plastic, graphite, metal (e.g., aluminum), or the like, or a combination thereof.

The aperture device 346 (also referred to herein as a collimator 346) may be configured to limit radiation beams emitted from the radiation source 320. For example, the aperture device 346 may prevent at least one portion of radiation beams emitted from the radiation source 320 from being incident on the subject (e.g., human tissue). Alternatively or additionally, the aperture device 346 may be configured to shape the radiation beams to a predetermined shape (or profile), for example, fan-shaped radiation rays. The predetermined shape may vary according to the different anatomy of the subject (for example, head, chest, etc.). The radiation beams collimated by the aperture device 346 may be projected to at least one portion of the subject. An area formed by the projected radiation beams may comply with the shape of the at least one portion of the subject to prevent other portions of the subject from being radiated. In some embodiments, the aperture device 346 may be configured to form an aperture in a specific shape. Radiation beams traversing the aperture in the specific shape may be collimated to be the predetermined shape corresponding to the specific shape of the aperture.

The second filter 348 may be configured to adjust the distribution of radiation rays that impinge upon the subject. The second filter 348 may be configured between the aperture device 346 and the bore 350. In some embodiments, the second filter 348 may be integrated into a cover encompassing the bore 350. The radiation rays adjusted by the second filter 348 may have a uniform intensity after being absorbed by the subject. The second filter 348 may include a bowtie filter, and/or a wedge filter, etc. In some embodiments, the thickness of the second filter 348 may decrease along a direction from an edge to a center of the second filter 348. For example, if most of the imaging mass (or a region of interest) of the subject is located at the center of the bore 350, the thickness of second filter 348 at the center may be the minimal and the thickness of second filter 348 at the edge may be greater than the thickness of the second filter 348 at the center. In some embodiments, the second filter 348 may include a third surface facing the aperture device 346 and a fourth surface facing the bore 350. The shape of the third surface of the second filter 348 (i.e., the top surface of the second filter 348) may conform to the shape of the aperture device 346, such as an arc-shape (e.g., the arc-shape shown in FIG. 3). The shape of the fourth surface of the second filter 348 (i.e., the bottom surface of the second filter 348) may conform to a shape of the bore 350. In some embodiments, the second filter 348 may include or be made of a second material capable of absorbing radiation, which may include at least one of plastic, graphite, metal (e.g., aluminum), or the like, or any combination thereof. The second material may be the same as or different from the first material. For example, the first filter 342 may include plastic, and the second filter 348 may include aluminum. As another example, the first filter 342 and the second filter 348 may both include graphite.

In some embodiments, the height of the collimator assembly 300 (denoted H in FIG. 3) may range from 8 to 20 cm. In some embodiments, the range of the height of the collimator assembly 300 may be restricted in a sub-range of 5.5 to 17.5 cm or 5 to 17 cm.

The collimator assembly 300 may be located between the radiation source 320 and the bore 350. The first filter 342 may be located between the radiation source 320 and the aperture device 346, and the second filter 348 may be located between the aperture device 346 and the bore 350. There may be a physical clearance between the second filter 348 and the bore 350 so that the collimator assembly 300 may move or rotate relative to the bore 350. In some embodiments, the collimator assembly 300 may move or rotate with the radiation source 320 by rotating the gantry of the imaging system 100.

In some embodiments, the collimator assembly 300 may include a measurement component. The measurement component may be configured to, for example, determine at least one of the intensity of radiation beams that reaches the first filter 342 or the location of the radiation source 320. In some embodiments, the measurement component may include an intensity sensor (e.g., an x-ray power meter, or an x-ray energy meter), a position sensor (e.g., a position sensitive detector), or the like, or any combination thereof. For example, the x-ray power meter may include a probe, for example, a thermal probe and/or a photodiode probe, to detect the radiation beams from the radiation source. As another example, the position sensitive detector may include a photoconductive detector, a photovoltaic detector, a Schottky barrier diodes detector, etc. In some embodiments, the measurement component may include one or more detectors that may be similar or same as the detector 250.

For example, the measurement component may include one single detector configured to detect the intensity of radiation beams that reaches the first filter 342. As another example, the measurement component may include several detectors arranged in an array or matrix. The several detectors arranged in an array or matrix may be configured to measure both intensity of radiation beams that reaches the first filter 342 and the location of the radiation source 320. The measurement component may be located a suitable place in the collimator assembly 300. For example, the measurement component may be located in the space in the first filter 342, such as in the concave formed by the first surface of the first filter 342 (i.e., the top surface of the first filter 342).

In some embodiments, the collimator assembly 300 may include a motion component (not shown). The motion component may be configured to move one or more components of the collimator assembly 300, such as the aperture device 346, the first filter 342, and/or the second filter 348. The motion component may move the aperture device 346, the first filter 342, and the second filter 348 separately or simultaneously. In some embodiments, the motion component may be integrated as an overall motion device with the rotation of one or more other components of the imaging system 100, for example, the gantry.

It should be noted that the collimator assembly 300 described above is provided for illustration, not intended to limit the scope of the present disclosure. For persons having ordinary skill in the art, multiple variations and modifications may be reduced to practice in the light of the present disclosure. However, those variations and modifications do not depart from the scope of the present disclosure. For example, the collimator assembly 300 may further include a flat filter (not shown in FIG. 3) in addition to the first and second filters. The flat filter may be configured to reduce particular radiation ray energies that are not ideal for imaging and harmful to the subject (e.g., human tissue). As another example, the second filter 348 may be omitted. In some embodiments, the first filter 342 may be configured in the collimator assembly 300 in a configuration that is different from that shown in FIG. 3. For example, the first surface of the first filter 342 described above (e.g., the descriptions of the shape and/or size thereof) may face the aperture device 346, and the second surface of the first filter 342 may face the radiation source 320. The first surface of the first filter 342 may bulge toward the radiation source 320. In some embodiments, instead of being part of the collimator assembly 300, the second filter 348 may be integrated into the bore 350.

Figure 4:
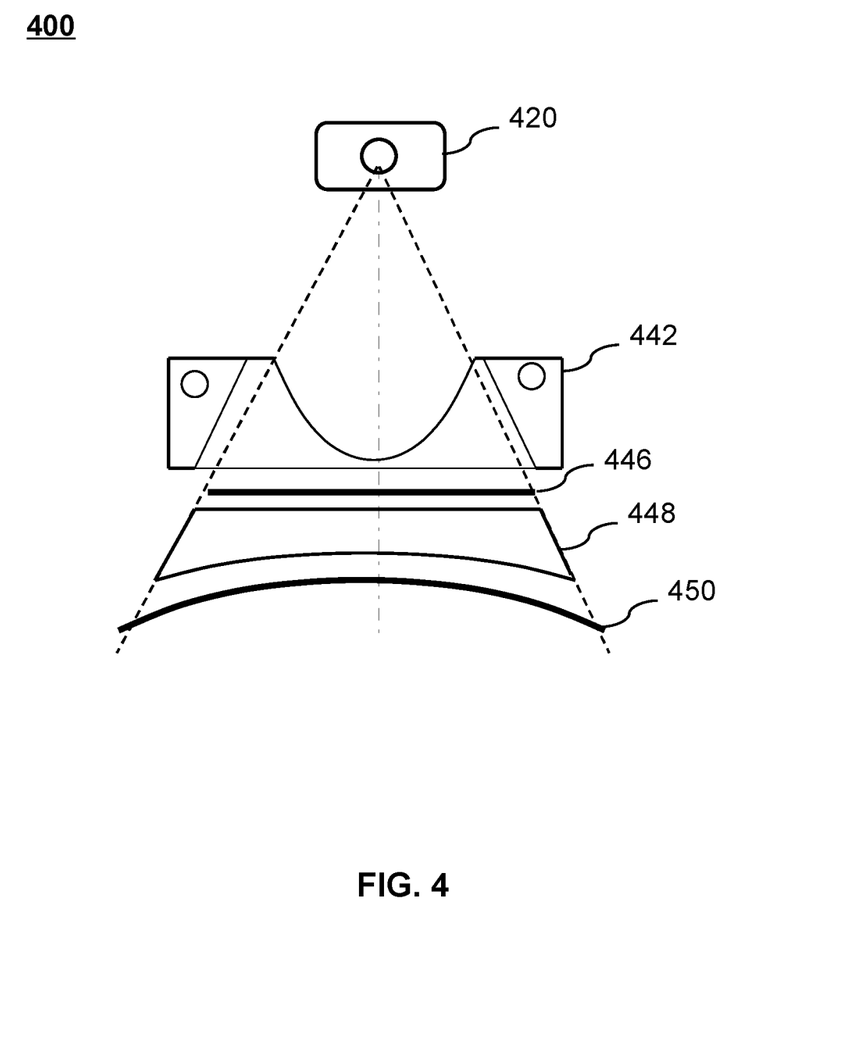
FIG. 4 is a schematic diagram illustrating an exemplary collimator assembly according to some embodiments of the present disclosure.

FIG. 4 is a schematic diagram illustrating an exemplary collimator assembly 400 according to some embodiments of the present disclosure. For brevity, a radiation source 420 and a bore 450 may be used for describing the collimator assembly 400. As illustrated in FIG. 4, the collimator assembly 400 may include a first filter 442, an aperture device 446, and a second filter 448, which are respectively similar to the first filter 342, the aperture device 346, and the second filter 348 described above in connection with FIG. 3. For example, the first filter 442 may include or be made of the material capable of absorbing radiation as the first filter 342. As another example, the first filter 442 and/or the second filter 448 may include a bowtie filter as the first filter 342 and/or the second filter 348.

The first filter 442 may include a first surface, which faces the radiation source 420 (i.e., the top surface of the first filter 442), and a second surface, which faces the aperture device 446 (i.e., the bottom surface of the first filter 442). The shape of the second surface may conform to the shape of the aperture device 446. The second filter 448 may include a third surface, which faces the aperture device 446 (i.e., the top surface of the second filter 448), and a fourth surface, which faces the bore 450 (i.e., the bottom surface of the second filter 448). The shape of the third surface of the second filter 448 may conform to the shape of the aperture device 446. The shape of the fourth surface of the second filter 448 may conform to the shape of the bore 450.

The collimator assembly 400 illustrated in FIG. 4 and the collimator assembly 300 illustrated in FIG. 3 may differ in the configurations of their components (e.g., the shapes and/or sizes of the first filter, aperture device, and/or second filter). For example, the shapes of the first filter 342 and the first filter 442 may be different; the shapes of the aperture device 346 and the aperture device 446 may be different; and/or the shapes of the second filter 348 and the second filter 448 may be different. For example, the aperture device 346 of the collimator assembly 300 may include a curve shape, and the second surface of the first filter 342 and the third surface of the second filter 348 may also be curved. On the other hand, the aperture device 446 of the collimator assembly 400 may include a flat shape, and the second surface of the first filter 442 and the first surface of the second filter 448 may both be flat.

Figure 5:
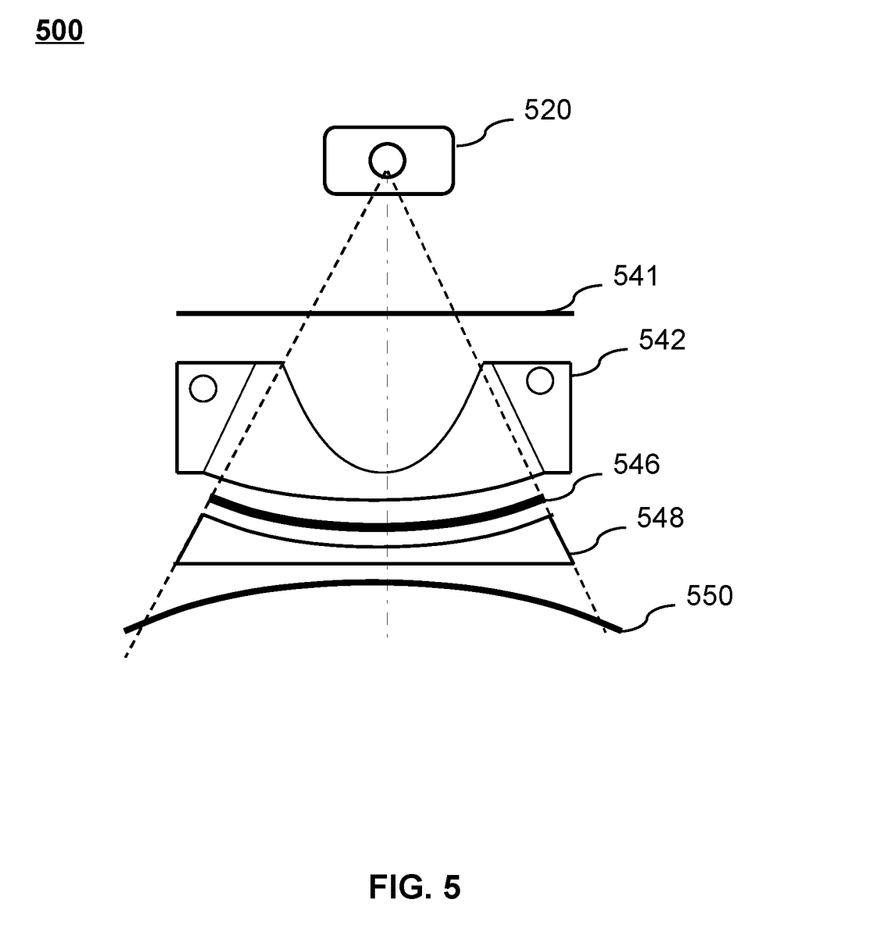
FIG. 5 is a schematic diagram illustrating an exemplary collimator assembly according to some embodiments of the present disclosure.

FIG. 5 is a schematic diagram illustrating an exemplary collimator assembly 500 according to some embodiments of the present disclosure. For brevity, a radiation source 520 and a bore 550 may be used for describing the collimator assembly 500. As illustrated in FIG. 5, the collimator assembly 500 may include a filter 541 (also referred to herein as a third filter 541), a first filter 542, an aperture device 546, and a second filter 548, which are respectively similar to the first filter 342, aperture device 346, and second filter 348 described above in connection with FIG. 3. For example, the material of the first filter 542 may be the same as the first filter 342. As another example, the shape and/or size of the second filter 548 may be the same as the shape and/or size of the second filter 348.

The collimator assembly 500 illustrated in FIG. 5 and the collimator assembly 300 illustrated in FIG. 3 differ in the configurations of their components (e.g., the shapes and/or sizes of the first filter, aperture device, and/or second filter). For example, the collimator assembly 500 may further including a third filter 541. The third filter 541 may be located between the radiation source 520 and the first filter 542. The third filter 541 may be configured to reduce particular energies of radiation rays that are not ideal for imaging or harmful to a subject (e.g., a human tissue). In some embodiments, the third filter 541 may include any shape, such as a flat shape (as shown in FIG. 5). In some embodiments, the third filter 541 may include or be made of a material that can remove a part of the radiation rays and/or absorb another part of the radiation rays, which may include plastic, graphite, metal (e.g., aluminum), or the like, or any combination thereof. The material of the third filter 541 may be the same as or different from the materials of the first filter 542 and/or the second filter 548.

Figure 6:
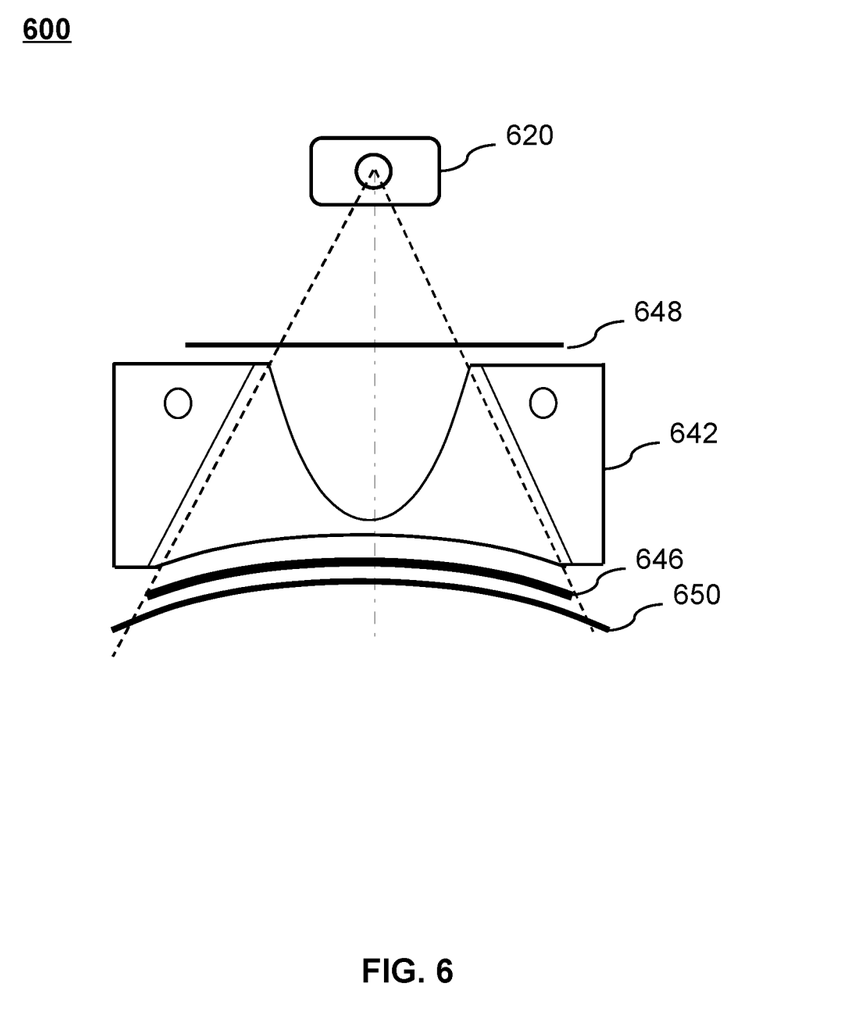
FIG. 6 is a schematic diagram illustrating an exemplary collimator assembly according to some embodiments of the present disclosure.

FIG. 6 is a schematic diagram illustrating an exemplary collimator assembly 600 according to some embodiments of the present disclosure. For brevity, a radiation source 620 and a bore 650 may be used for describing the collimator assembly 600. As illustrated in FIG. 6, the collimator assembly 600 may include a first filter 642, an aperture device 646, and a third filter 648, which are respectively similar to the first filter 342, aperture device 346 described above in connection with FIG. 3. For example, the first filter 642 may include or be made of the material capable of absorbing radiation as the first filter 342. As another example, the first filter 642 may include a bowtie filter as the first filter 342.

The first filter 642 may include a first surface, which faces the radiation source 620 (i.e., the top surface of the first filter 642), and a second surface, which faces the aperture device 646 (i.e., the bottom surface of the first filter 642). The shape of the second surface may conform to the shape of the aperture device 646.

The collimator assembly 600 illustrated in FIG. 6 and the collimator assembly 300 illustrated in FIG. 3 may differ in the configurations of their components (e.g., the shapes and/or sizes of the first filter, aperture device, and/or second filter). For example, the shape of the aperture device 646 of the collimator assembly 600 may conform to the shape of the bore 650, and the second surface of the first filter 642 may form a convex as shown in FIG. 6. On the other hand, the second surface of the first 342 may form a concave as shown in FIG. 3. As another example, the collimator assembly 300 may include a second filter 348 between the aperture device 346 and the bore 350. On the other hand, the collimator assembly 600 may include a filter between the aperture device 646 and the bore 650, and may include a third filter 648 between the radiation source 620 and the first filter 642. The third filter 648 may be configured to reduce particular energies of radiation rays that are not ideal for imaging or harmful to a subject (e.g., human tissue) with any shape, such as a flat shape (as shown in FIG. 6). In some embodiments, the third filter 648 may include or be made of a material that can remove a part of the radiation rays and/or absorb another part of the radiation rays, which may include plastic, graphite, metal (e.g., aluminum), or the like, or any combination thereof. The material of the third filter 648 may be the same as or different from the material of the first filter 642. For instance, the first filter 642 may include plastic and the third filter 648 may include aluminum, or the first filter 642 and the third filter 648 may both include graphite.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code) or combining software and hardware implementation that may all generally be referred to herein as a "unit," "module," or "system." Furthermore, aspects of the present disclosure may take the form of a computer program product embodied in one or more computer readable medium having computer readable program code embodied thereon.

A computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including a subject-oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A device, comprising:
a collimator positioned between a radiation source of a scanner and a bore of the scanner, the bore including a detecting region configured to accommodate a subject, the collimator being configured to prevent at least one portion of radiation rays emitted from the radiation source from being incident on the subject; and
a filter positioned between the collimator and the bore, the filter including a first surface facing the collimator with a shape conforming to a shape of the collimator and a second surface facing the bore with a shape conforming to a shape of the bore, wherein a height of the device ranges from 5.5 to 17.5 centimeters or ranges from 5 to 17 centimeters, and a thickness of the filter decreases along a direction from an edge to a center of the filter.

2. The device of claim 1, wherein the filter includes at least one of a bowtie filter or a wedge filter.

3. The device of claim 1, wherein the filter is integrated into a cover encompassing the bore.

4. The device of claim 1, further comprising a first filter positioned between the radiation source and the collimator, wherein the collimator is between the first filter and the filter.

5. The device of claim 4, wherein the first filter includes a surface facing the collimator with a shape conforming to the shape of the collimator and a surface facing the radiation source, the surface facing the radiation source forming a concave.

6. The device of claim 5, further comprising a measurement component, wherein the measurement component being configured to determine at least one of an intensity of radiation beams that reaches the first filter or a location of the radiation source.

7. The device of claim 6, wherein the measurement component is located in the concave.

8. The device of claim 4, wherein the first filter device includes at least one of a bowtie filter or a wedge filter.

9. The device of claim 4, wherein a material of the filter or the first filter includes at least one of plastic, graphite, or aluminum.

10. The device of claim 4, further comprising a motion component configured to move at least one of the collimator, the filter, or the first filter.

11. The device of claim 1, wherein the filter has a minimal thickness at the center.

12. A device, comprising:
a collimator positioned between a radiation source of a scanner and a bore of the scanner, the bore including a detecting region configured to accommodate a subject, the collimator being configured to prevent at least one portion of radiation rays emitted from the radiation source from being incident on the subject; and;
a first filter positioned between the radiation source and the collimator, the filter including a first surface facing the radiation source and a second surface facing the collimator, wherein the first surface forms a concave and a shape of the second surface conforms a shape of the collimator, and the first filter includes at least one of a bowtie filter or a wedge filter.

13. The device of claim 12, further comprising a measurement component accommodated in the concave, the measurement component being configured to determine at least one of an intensity of radiation beams that reaches the first filter or a location of the radiation source.

14. The device of claim 12, further comprising a second filter located between the collimator and the bore.

15. The device of claim 14, wherein the second filter includes a surface facing the collimator with a shape conforming to a shape of the collimator and a surface facing the bore with a shape conforming to a shape of the bore.

16. The device of claim 15, wherein a height of the device ranges from 5.5 to 17.5 cm or ranges from 5 to 17 cm.

17. The device of claim 14, wherein the second filter includes at least one of a bowtie filter or a wedge filter.

18. A device, comprising:
a collimator positioned between a radiation source of a scanner and a bore of the scanner, the bore including a detecting region configured to accommodate a subject, the collimator being configured to prevent at least one portion of radiation rays emitted from the radiation source from being incident on the subject;
a first filter being a bowtie filter positioned between the radiation source and the collimator; and
a second filter being a flat filter positioned between the radiation source and the first filter.

19. The device of claim 18, wherein the first filter includes a first surface facing the radiation source and a second surface facing the collimator, the first surface forming a concave and a shape of the second surface conforming a shape of the collimator.

20. The device of claim 18, further comprising a third filter positioned between the collimator and the bore, wherein the third filter includes a surface facing the collimator with a shape conforming the collimator and a surface facing the bore with a shape conforming the bore.

* * * * *